ID: 190,974

United States Patent [19]
Mück et al.

[11] 4,353,856
[45] Oct. 12, 1982

[54] PROCESS AND EMBEDDING SYSTEM FOR EMBEDDING TISSUE SAMPLES

[75] Inventors: Karl-Friedrich Mück, Wiesbaden; Lothar Post, Kelkheim; Hannes Westen, Wiesbaden, all of Fed. Rep. of Germany

[73] Assignee: Hoechst Aktiengesellschaft, Frankfurt am Main, Fed. Rep. of Germany

[21] Appl. No.: 190,974

[22] Filed: Sep. 26, 1980

[30] Foreign Application Priority Data

Sep. 29, 1979 [DE] Fed. Rep. of Germany ....... 2939582

[51] Int. Cl.$^3$ ....................... G01N 31/00; A01N 1/00
[52] U.S. Cl. .................. 264/240; 264/279.1; 427/2; 424/3
[58] Field of Search .......................... 424/3; 427/2, 4; 264/240, 279.1

[56] References Cited

U.S. PATENT DOCUMENTS 4,120,991 10/1978 Ornstein ................................. 427/2

OTHER PUBLICATIONS

C.A., vol. 74, 1971, 121242s.

*Primary Examiner*—Sam Silverberg
*Attorney, Agent, or Firm*—Curtis, Morris & Safford

[57] ABSTRACT

The invention relates to a process and an embedding system for embedding tissue samples in a mixture of a hydroxyalkyl (meth)acrylate and an alkyl (meth)acrylate in a weight ratio of at most 9:1. The embedding process takes place at low temperatures using a low-temperature initiator system. It is thereby possible largely to retain the enzyme activity and the cell morphology.

6 Claims, No Drawings

PROCESS AND EMBEDDING SYSTEM FOR EMBEDDING TISSUE SAMPLES

The present invention relates to a process for embedding tissue samples, for enzyme histochemistry, in mixtures of a hydroxyalkyl (meth)acrylate and an alkyl (meth)acrylate at low temperatures.

It is known that monomeric methyl methacrylate (MMA) can be used for embedding tissue samples for microscopic cell investigation; compare Mikroskopie 13, page 386 (1959). This embedding in MMA is at present the preferred method for the fine-tissue investigation of bone-marrow biopsies performed on humans and animals, since the prior decalcification, of the bony constituents of the tissue, which would otherwise be required is not necessary in this method.

However, a considerable disadvantage of the currently known MMA embedding processes is that only a very limited number of enzyme histochemical detections which are known from the literature can be carried out on tissue samples prepared in this manner. These detections so far include the detection of the activity of $\alpha$-naphthol-AS-D-chloracetate esterase and acid phosphatase. A reason for the difficulty of detecting sensitive cell enzymes in tissue samples embedded in MMA is, inter alia, that the embedding process hitherto used proceeds under conditions under which most enzymes lose their activity.

A process for embedding tissue, for enzyme histochemistry, which is based on 2-hydroxyethyl methacrylate, a water-soluble methacrylate, has been disclosed (compare Beitr. path. Anat. 147, page 201 (1972)). However, this embedding process has, above all, the two following disadvantages: Firstly, since the embedding material is hygroscopic, the specimens obtained by this process can be handled only with difficulty and, in particular, are difficult to cut. Secondly, embedding mixtures based on these water-soluble methacrylates are unsuitable, for example, for bone-marrow histology since, in the case of relatively large tissue samples containing bone, it is impossible to achieve uniform polymerization over the entire cross-section of the sample, using these mixtures.

A process for embedding tissue samples in which the sample is embedded by polymerization in methyl methacrylate, optionally mixed with other (meth)acrylates and/or a plasticizer, at temperatures of at most $+15°$ C. in the presence of a low-temperature initiator system containing an accelerator in addition to the agent which forms free radicals, has already been proposed in German patent application No. P 28 47 974.5. This patent application also relates to embedding systems of the appropriate composition. The disadvantage of this process is, inter alia, that the application to glass slides is usually relatively difficult.

It has now been found that when mixtures of alkyl (meth)acrylates and hydroxyalkyl (meth)acrylates are used, advantageous results can be achieved and the disadvantages of the above state of the art can be entirely, or at least largely, avoided.

The invention thus relates to a process for embedding tissue samples, in particular of tissue with bony constituents, in which the sample is embedded by polymerization in an alkyl (meth)acrylate, optionally mixed with a plasticizer, at temperatures of at most $+20°$ C., preferably at $+2°$ C. to $-20°$ C., in the presence of a low-temperature initiator system which is in itself known and contains an accelerator in addition to the agent which forms free radicals, which comprises using the alkyl (meth)acrylate as a mixture with a hydroxyalkyl (meth)acrylate, the weight ratio of hydroxyalkyl (meth)acrylate to alkyl (meth)acrylate not exceeding the value of 9:1.

According to the invention, a mixture of a hydroxyalkyl (meth)acrylate and/or a hydroxyalkyl acrylate as one monomer component and an alkyl methacrylate and/or alkyl acrylate as the other monomer component thus serves as the embedding medium. The mixing ratio is preferably between 8:2 and 4:6 parts by weight, and in particular between 3:1 and 1.5:1.

The particular acrylate or the corresponding acrylate polymer thereby acts as a plasticizer for the remainder of the polymer phase. The monomer mixture according to the invention thus preferably contains at least one acrylic monomer, that is to say either an alkyl acrylate or hydroxyalkyl acrylate. If this is not the case, that is to say if only methacrylates are used as monomers, suitable additives (plasticizers) must in general be added in order to obtain an embedded composition which can be cut sufficiently easily.

It is expedient for the hydroxyalkyl radical in the hydroxyalkyl (meth)acrylate, which is preferably a 2-hydroxyalkyl (meth)acrylate, to contain 2 to 6 C atoms, preferably 2 to 4 C atoms, examples which may be mentioned being 2-hydroxyethyl, 2-hydroxypropyl, 2-hydroxy-n- or -i-butyl and 2-hydroxy-n-hexyl. 2-Hydroxypropyl (meth)acrylate and 2-hydroxybutyl (meth)acrylate, and in particular 2-hydroxyethyl methacrylate or 2-hydroxyethyl acrylate, are preferably used according to the invention. Both mixtures of the various hydroxyalkyl methacrylates and hydroxyalkyl acrylates amongst themselves, and mixtures with one another are possible.

Suitable alkyl (meth)acrylates are, above all, those with 1 to 10 C atoms, preferably 1 to 6 C atoms, in the alcohol component. Both mixtures of the various alkyl methacrylates and alkyl acrylates amongst themselves, and mixtures with one another are also possible in this case. Examples of alkyl methacrylates which may be mentioned are methyl methacrylate, ethyl methacrylate, propyl methacrylate and butyl methacrylate, methyl methacrylate being preferred; with regard to the acrylates, ethyl acrylate, propyl acrylate, butyl acrylate and n-hexyl acrylate may be mentioned above all. In the case of mixtures of methacrylates and acrylates, the corresponding acrylate polymer again has the effect of plasticizing the polymer phase.

The above monomers usually contain the known stabilizers (polymerization inhibitors), such as p-hydroquinone, which can, if necessary, be removed by known methods, such as, for example, by distillation or by column chromatography, before the start of polymerization. However, this is generally not necessary, the stabilizer rather being compensated in this case by an appropriately larger amount of free radical initiator.

The embedding mixture according to the invention preferably contains substances which have a plasticizing effect (plasticizers). Possible substances of this type are, on the one hand, the hydroxyalkyl acrylates and/or alkyl acrylates, or the corresponding polymers, such as have already been listed above. On the other hand, compounds of the type described, for example, in the journal "Blut," volume XIII, book 6 (September 1966), page 337 et seq., in particular pages 345 and 355, are also suitable for this purpose. Preferred compounds which may be mentioned in this context are nonylphenol polyglycol ether-acetate and butylglycol. Mixtures of these compounds with the hydroxyalkyl acrylates or alkyl acrylates mentioned are also possible. Depending on the nature of the plasticizer, the amount of plasticizer is usually between 3 and 30% by weight, relative to the monomer mixture.

The low-temperature initiator systems in the context of the invention consist of (a) the agents which form free radicals (free radical initiators) and which are customary for the polymerization of acrylates and (b) an accelerator (co-initiator).

Possible free radical initiators are the compounds known for this purpose, for example peroxy compounds, such as organic peroxides and hydroperoxides or percarbonates. Examples which may be mentioned in this context are dibenzoyl peroxide, dilauryl peroxide, tert.-butyl perpivalate and diisopropyl percarbonate. Mixtures of such free radical initiators can also be used. Because free radical initiators of this type as a rule have a favorable solubility in alkyl (meth)acrylates, in particular methyl methacrylate, it can be advantageous first to prepare an appropriate solution and then to add this solution to the remaining components.

The accelerators used according to the invention are the compounds known for this purpose, such as, for example, straight-chain or branched, secondary or tertiary aliphatic amines, preferably with 1-5 C atoms, aliphatic-cycloaliphatic secondary or tertiary amines and aromatic-aliphatic secondary or tertiary amines.

Tertiary amines are the preferred amines. Examples of these which may be mentioned are: triethylamine, N,N-dimethylaniline, N,N-diethylaniline and N,N-dimethyl-p-toluidine. The use of mixtures of these accelerators is, of course, also within the scope of the invention.

Other examples of low-temperature initiator systems which can be employed according to the invention are described, for example, in Houben-Weyl, "Methoden der organischen Chemie" ("Methods of Organic Chemistry"), volume 14/1 (1961), page 263 et seq. and page 291 et seq. (Thieme-Verlag, Stuttgart).

The combination of dibenzoyl peroxide with one of the above tertiary amines and one of the polymerization regulators listed below is preferably used, according to the invention, as the low-temperature initiator system.

The amount of initiator system according to the invention and of the individual components depends on the nature of the particular initiator system or of the individual components, on the desired polymerization time, on the polymerization (embedding) temperature and on the amount of hydroxyalkyl (meth)acrylate, but can easily be determined by simple routine experiments. Thus, if the same initiator system is used, more of this system must of course be used the lower the temperature is, in order to achieve an embedding time which is still acceptable. On the other hand, at higher temperatures, correspondingly less initiator system is to be used so that there is no danger of the temperature of the sample rising too much above the ambient temperature, because the polymerization is too rapid, and thus of damage occurring to the enzyme activity. Furthermore, the higher is the content of hydroxyalkyl (meth)acrylate, the lower the amount of initiator system can be.

According to the invention, the amount of free radical initiator is in general 5% to 0.5%, preferably 3.5% to 1%, and that of the accelerator is in general 10% to 0.1%, preferably 0.5% to 0.1%, in each case relative to the monomer mixture.

The abovementioned ranges are in themselves not critical and the amounts used can be less or greater within certain limits, although certain disadvantages must then as a rule be accepted.

Thus, as mentioned, the temperature has a decisive influence on the limiting ranges of the initiator system according to the invention; that is to say if low temperatures and small amounts of initiator are simultaneously used, only a delayed or incomplete polymerization takes place if less than a certain amount, which can easily be determined, of the total initiator or of a component of the initiator is employed.

On the other hand, amounts of the total initiator, and in particular of the co-initiator, which are too high can lead to diffusion disorders in the center of the tissue samples, these disorders under certain circumstances being accompanied by crosslinking phenomena in the polymer. This effect can interfere with the further processing of the samples, for example during cutting of the blocks of plastic or during the dissolving of the plastic out of the tissue sections, which may be necessary later for staining. In this respect, for example, if DMA and a temperature of, for example, +2° C. are used, the amount of DMA should, as far as possible, not exceed 0.9%, relative to the monomer mixture.

Moreover, as already mentioned, the danger of damage to the sample by heat is greater with high amounts of initiator.

In addition to the abovementioned accelerators, heavy metal salts can also be employed as accelerators if necessary, especially at embedding temperatures below 0° C. These heavy metal salts are preferably those which are soluble in the monomer and in which the heavy metal ion can undergo a change in valency, such as, for example, cobalt salts, copper salts, vanadium salts or iron salts. In certain circumstances it is also possible to employ the heavy metal salt instead of the accelerators mentioned.

It has proved particularly advantageous to use so-called polymerization regulators in addition to the accelerators, since a more uniform course of polymerization, avoiding temperature peaks, is achieved in this manner. In addition, the amount of initiator system can thereby be correspondingly reduced.

Examples of possible polymerization regulators of this type are organic phosphorus compounds and, above all, organic sulfur compounds. The former compounds include, in particular, aliphatic or aromatic secondary or tertiary phosphines, such as, for example, triphenylphosphine. Amongst the organic sulfur compounds there may be mentioned, in particular, mercaptans or thiophenols, preferably those with a low volatility, or sulfones such as are described, for example, in German Pat. No. 916,733. Examples which may be mentioned in this context are: dodecylmercaptan, thiophenol, thiocresol and β-hydroxyethyl p-tolyl sulfone.

Furthermore, solvents, and in particular above all aliphatic monohydric alcohols with 1 to 6 C atoms, such as methanol, ethanol, n- and i-propanol and n- and i-butanol, are also possible polymerization regulators. Aliphatic ketones, in particular those with 3 to 6 C atoms, such as acetone and methyl ethyl ketone, are also suitable for this purpose. Mixtures of the various solvents can also be used.

It is expedient to use the heavy metal salts and polymerization regulators in amounts of 0.05 to 2%, preferably 0.01 to 1%, relative to the monomer mixture. If the polymerization regulators are solvents, the amount thereof is as a rule 5 to 20%, preferably 10-15%, also relative to the monomer mixture.

The temperatures at which, according to the invention, the embedding process takes place are sufficiently low for the enzyme activity of the particular tissue sample to be completely or at least largely retained, that is to say as a rule −40° C. to at most +20° C., preferably +2° C. to −20° C.

Whilst the upper limit of the temperature is determined by the increase in damage to the enzyme activity, the lower limit of the temperature is determined by the decreasing activity of the initiator system according to the invention at low temperature and the rise in the polymerization time resulting therefrom. In most cases, temperatures below about −50° C. should therefore scarcely be used in practice.

The temperatures stated are understood as the temperature of the particular cooling medium, for example of the ice-bath or of the refrigerator. Care should therefore be taken, by a suitable polymerization procedure, that the temperature of the polymerization mixture and of the sample to be embedded does not rise considerably above this ambient temperature.

In the case of an appropriately active initiator system, correspondingly lower amounts thereof, for example, are thus to be employed, and vice versa, or a sufficiently low ambient temperature is to be chosen, or the amount of polymerization regulator is to be metered appropriately. If necessary, a rise in temperature in the embedding mixture can also be counteracted by appropriately intense cooling.

If necessary, the temperature of the embedding mixture can be monitored by customary temperature probes.

This is preferably effected by a fine measuring electrode of an iron/constantan thermoelement (for example from Messrs. Degussa) immersed in a methanol-filled test-tube (for example No. 39/10 A from Messrs. Sarstedt). The measured voltage, calibrated in degrees centigrade, of the thermoelement can preferably be recorded with a line recorder (for example PM 8010 from Messrs. Philips).

To carry out the embedding process according to the invention, the particular tissue sample is first pre-treated in the customary manner, that is to say, for example, fixed and dehydrated, as described, for example, in the literature reference quoted above or in "Blut," volume 32 (1976) pages 215-218 and in "Beitr. path. Anat.," volume 147 (1972) pages 201-206.

The sample pre-treated in this manner is then introduced into the embedding mixture according to the invention, which may already contain one of the two initiator components, and, after adding the low-temperature initiator or the other particular initiator component and, if appropriate, the additional accelerator and/or polymerization regulator, the embedding by polymerization is then carried out. It is not necessary to carry out the reaction in the absence of oxygen, although this procedure is preferred according to the invention. In the presence of oxygen, care must be taken that not too much oxygen is introduced into the embedding mixture during mixing of the various constituents of the embedding mixture, since otherwise disorders in the course of polymerization and damage to the specimen can occur.

The embedding process is carried out in a mold customary for this purpose, for example in a small glass tablet tube with an internal diameter of, for example, 25 mm and a stopper.

The polymerization time depends, above all, on the particular initiator system chosen and the temperature and is in general 8 to 56 hours, preferably 6 to 48 hours, depending on the amount of hydroxyalkyl (meth)acrylate. If soft tissue samples are being embedded, these times are appropriately shorter.

The embedded tissue samples obtained in the form of blocks of plastic are then cut in the customary manner (hard section technique), and if necessary freed from polymeric embedding material by dissolving this in suitable solvents, such as, for example, ketones, (acetone), chlorinated hydrocarbons (chloroform), aromatic solvents (benzene or toluene) or esters (methylglycol acetate) and stained, and are then tested for the various tissue enzymes (for example alkaline phosphatase) by the known methods of detection. With regard to the known process methods used here, reference may be made, for example, to R. Burkhardt, "Farbatlas der klinischen Histopathologie von Knochenmark und Knochen" ("Color Atlas of Clinical Histopathology of Bone-Marrow and Bone") (1970), Springer Verlag or R. Burkhardt in "Blut," volume XIII (6), September 1966, page 338 et seq. and to T. BARKA and P. J. ANDERSON: "Histochemistry: Theory, Practice and Bibliography", Hoeber Medical Division, Harper & Row Inc., New York (1963).

In a preferred embodiment of the process according to the invention, the appropriately pre-treated tissue sample is introduced into the embedding mixture containing the free radical initiator, the co-initiator and the polymerization regulator, this mixture first having been cooled to temperatures below −10° C., preferably below −15° C., for example −15° C. to −25° C. The polymerization is then likewise carried out at these temperatures and as a rule extends over a period of several days, depending on the particular nature of the initiator system. In this procedure, virtually only impregnation of the tissue sample initially takes place in the first hours, since in this phase polymerization does not yet proceed to an appreciable extent. Since this process variant is carried out, in particular, at low temperatures, it enables larger amounts of initiator to be employed, which has a favorable effect on the cell morphology of the sample.

In another preferred embodiment of the process according to the invention, the tissue sample is first treated with the embedding mixture containing only one of the two initiator components, preferably the accelerator, the concentration of this one initiator component being higher, preferably 2 to 10 times higher and in particular 8 to 10 times higher, than in the actual embedding mixture containing both initiator components. When DMA is used, in particular, as the accelerator, a concentration range of 1% to 5%, relative to the monomer mixture in the impregnating system, and 0.05% to 0.2%, relative to the monomer mixture in the embedding system, has proved advantageous.

The impregnation temperature, impregnation time and size of the tissue samples are closely related such that lower temperatures and larger pieces of tissue automatically give rise to longer times, and vice versa. In principle, the impregnation temperature is in the same range as the embedding temperature according to the invention, that is to say it is at most +15° C. However, temperatures below +15° C., for example between 0° C. and +4° C., are preferred. The impregnation time in this case is about 4 to 6 hours for a bone-marrow biopsy sample about 4×20 mm in size.

In the case of tissues with very high bone contents or in the case of bone constituents which are particularly compact as a result of the species from which they are taken (for example in the case of rats), under certain circumstances it is advisable to pre-impregnate the samples, after dehydration, with pure alkyl methacrylate, preferably methyl methacrylate, for 4 to 6 hours. In some cases, these pre-impregnation times can even be considerably longer for larger samples.

The actual polymerization is then also carried out in approximately the above temperature range, for example at 0° to +8° C. Compared with the first preferred variant mentioned, this second preferred variant has the advantage of a shorter polymerization time and hence a shorter embedding time, since higher temperatures can be used in this variant.

According to the invention, it is also possible to combine the two preferred variants above, and in particular to do so in a manner such that the impregnation is first carried out in the presence of the two initiator components at low temperatures according to the first variant and the temperature is then increased accordingly and the procedure of the second variant is followed. The initial impregnation of the tissue sample with a relatively high proportion of initiator according to the preferred variants described above ensures a particularly good microscopic cell morphology and to a very great extent prevents the formation of microscopic shrinkage artefacts in the tissue.

According to claim 9, the system, according to the invention, used for embedding tissue samples essentially consists of the initially separate components (a), (b) and (c), which are then brought together in an appropriate manner during the embedding process. If appropriate, component (a) can already contain some, for example 20 to 60%, or even all of the polymerization accelerator and/or polymerization regulator or, but less preferably, of the agent which forms free radicals. If component (a) already contains all of the polymerization accelerator or agent which forms free radicals, component (b) or (c) is, of course, eliminated.

In a preferred embodiment, some, for example 20 to 60%, or even all of the plasticizer is also already present in component (a).

For embedding tissue samples containing bone, the embedding system can also consist of components (a), (a)' and (b), (a) and (a)' already containing all the polymerization accelerator but the proportion of polymerization accelerator in component (a), with which the tissue sample is first treated, being higher, preferably 2 to 10 times higher, than the proportion in (a)'. It is also possible for all of the polymerization regulator and, preferably, of the plasticizer already to be present, in any desired distribution, in the two components (a) and (a)'.

Because the solubility of the free radical initiators employed according to the invention in the alkyl (meth)acrylate, in particular methyl methacrylate, is as a rule good, it can be advantageous to withdraw some, for example 20 to 60%, or all of the alkyl (meth)acrylate from component (a) of the embedding set as a component in its own right, that is to say component (d). This component (d) is then first mixed with the free radical initiator in question and the resulting solution is subsequently added to the remaining components.

The procedure according to the invention enables embedded tissue, in particular bone-containing tissue samples, to be prepared in a surprisingly simple manner with the enzyme activity and the cell morphology being largely retained, which is of considerable importance for enzyme-histochemical diagnostics. Non-uniform polymerization over the cross-section of the sample to be embedded and possible disorders in the polymerization in the center of the tissue samples, as well as an impairment to the cell morphology are avoided, especially in the preferred embodiments of the process according to the invention.

As a result of using an embedding medium containing a hydroxyalkyl (meth)acrylate, the sections obtained from the embedded tissue preparations according to the invention have the property of unassistedly spreading out on an aqueous surface, which considerably facilitates application to glass slides. In addition, the polymeric embedding material as a rule does not have to be dissolved out of the section before staining.

The procedure according to Example 4 which follows is at present regarded as the best embodiment of the invention.

Examples

The bone-containing tissue samples to be embeded (bone-marrow biopsy cylinders) were first fixed, and in particular, for the alkaline phosphatase reaction, for 2 to 4 hours in a mixture consisting of two parts of absolute methanol, one part of Formol (37% strength) and 3% of glucose phosphate buffer of pH 7.4. For the reaction for non-specific esterase and acid phosphatase, the fixation time was 2 to 6 hours in 4% strength paraformaldehyde, dissolved in 0.1 M cacodylate buffer of pH 7.2. The samples were then dehydrated in the course of 2 hours in 2-hydroxyethyl methacrylate, the dehydrating agent being changed 6 times, and were then treated with the impregnation mixture for at least 4 hours and fully polymerized with the embedding mixture in molds (flat-bottomed glass vessels of Illex brown glass from Münnerstädter Glaswarenfabrik catalog No. Wda 1/05 with an internal diameter of 25 mm and stoppers). The details for each particular case can be seen from the following table.

In the case of tissues with very high bone contents, the bone was pre-impregnated, after dehydration, with pure methyl methacrylate for about 4 hours.

The resulting embedded tissue samples, in the form of blocks of plastic, were then cut into tissue sections with the aid of a commercially available hard section microtome (rotary microtome No. 1140 from Messrs. R. Jung, Nussloch). After Giemsa staining, the morphological state of the tissue in the sections was examined microscopically. The enzyme activities were determined, also microscopically, on sections which had first been partly freed from the polymeric embedding material with methylglycol acetate and had been treated with reagents for various tissue enzymes. Positive enzyme activities were thereby obtained after incubating the sections at 37° C. for 90 minutes, and in particular positive enzyme activities for alkaline phosphatase (compare "Blood" volume 10, page 1,023, 1955), acid phosphatase with Fast Garnet GBC salt (compare J. Path. Bact. volume 64, page 627, 1952) and non-specific esterase (compare J. Histochem. Cytochem. volume 7, page 297, 1959).

The results are likewise shown in the following table.

TABLE

| No. | Impregnation mixture/ temperature (°C.) | Time (hours) | Embedding mixture/ temperature (°C.) | Maximum temperature (°C.) | Polymerization time (hours) | Remarks |
|---|---|---|---|---|---|---|
| 1 | 3 ml of MMA<br>7 ml of HEMA<br>1 ml of BUG<br>1% of A.182<br>3% of BPO<br>/+ 2° C. | 4 | 3 ml of MMA<br>7 ml of HEMA<br>1 ml of BUG<br>1% of A.182<br>0.05% of BPO<br>0.01% of DEA<br>/+ 2° C. | + 8° C. after 11 hours | about 14 | Homogeneously embedded samples which can be cut, enzyme activity can be detected and localized |
| 2 | 1.5 ml of MMA<br>8.5 ml of HEMA<br>0.5% of A.182<br>3% of BPO<br>2 ml of BUG<br>/+ 2° C. | 4 | 1.5 ml of MMA<br>8.5 ml of HEMA<br>1% of A.182<br>0.3% of BPO<br>0.1% of DMA<br>/+ 2° C. | + 10° C. after 8 hours | about 10 | Homogeneously embedded samples which can be cut, enzyme activity can be detected and localized |
| 3 | 1.0 ml of MMA<br>6.0 ml of HEMA<br>3.0 ml of BA<br>3% of BPO<br><br>/+ 2° C. | 4 | 1.0 ml of MMA<br>6.0 ml of HEMA<br>3.0 ml of BA<br>0.3% of BPO<br>0.15% of DMA<br>0.5% of TPP<br>/+ 2° C. | + 9° C. after 8 hours | about 10 | Homogeneously embedded samples which can be cut, enzyme activity can be detected and localized |
| 4 | 3 ml of MMA<br>6 ml of HEMA<br>1 ml of HEA<br>1 ml of PROP<br>3% of BPO<br>/+ 2° C. | 4 | 3 ml of MMA<br>6 ml of HEMA<br>1 ml of HEA<br>1 ml of PROP<br>0.3% of BPO<br>0.15% of DMA<br>/+ 2° C. | + 20° C. after 8 hours | about 8 | Homogeneously embedded samples which can be cut, enzyme activity can be detected and localized |

DEA = N,N—diethylaniline
BPO = dibenzoyl peroxide
MMA = methyl methacrylate
HEMA = 2-hydroxyethyl methacrylate
HEA = 2-hydroxyethyl acrylate
BUG = butylglycol
DMA = N,N—dimethylaniline
A.182 = "Accelerator 182" from Messrs. Oxydo (polymerization regulator)
BA = butyl acrylate
TPP = triphenylphosphine
PROP = propanol

We claim:

1. In a process for embedding tissue samples in which the sample is embedded by polymerization, at temperatures of at most +20° C., of (meth)acrylate, optionally admixed with a plasticizer, in the presence of a low-temperature initiator system which contains an accelerator in addition to the agent which forms free radicals, the improvement of which comprises: treating first the tissue sample with a mixture of at least one monomer of an alkyl (meth)acrylate and a hydroxy alkyl (meth)acrylate, accelerator and/or agent which forms free radicals, the concentration of accelerator and/or agent which forms free radicals being greater in this first polymerization mixture than in a second polymerization mixture, said concentration of accelerator and/or agent which forms free radicals being at least 2 to 10 times higher than the concentration in the second polymerization mixture; further treating said tissue with the second polymerization mixture of an alkyl (meth)acrylate and a hydroxyalkyl (meth)acrylate, the weight ratio of hydroxyalkyl (meth)acrylate to alkyl (meth)acrylate in a mixture with said initiator system not exceeding the value of 9:1, and polymerizing said mixture whereby an embedded tissue is recovered.

2. The process as defined in claim 1, wherein the weight ratio of hydroxyalkyl (meth)acrylate to alkyl (meth)acrylate is 8:2 to 4:6.

3. The process as defined in claim 1, wherein tertiary aliphatic and/or aromatic-aliphatic amines and/or heavy metal salts are employed as the accelerators.

4. The process as defined in claim 1, wherein the temperature is +2° C. to −20° C.

5. The process as defined in claim 1, wherein nonylphenol polyglycol ether-acetate or butylglycol is employed as the plasticizer.

6. The process as defined in claim 1, wherein polymerization regulators are also additionally employed.

* * * * *